US005868027A

United States Patent [19]
Norton et al.

[11] Patent Number: 5,868,027
[45] Date of Patent: Feb. 9, 1999

[54] MEASUREMENT OF VISCOSITY OF A MELT IN A PLASMA CENTRIFUGAL FURNACE

[75] Inventors: Olin Perry Norton; Walter P. Okhuysen; William Steve Shepard; Carlson C. P. Pian, all of Mississippi State, Miss.

[73] Assignee: Mississippi State University, Mississippi State, Miss.

[21] Appl. No.: 724,008

[22] Filed: Sep. 30, 1996

[51] Int. Cl.$^6$ ............................ G01N 11/00; G01N 11/02
[52] U.S. Cl. .......................... 73/54.01; 73/54.02
[58] Field of Search ................. 73/54.01, 54.02

[56] References Cited

U.S. PATENT DOCUMENTS

| 5,187,975 | 2/1993 | Chiba et al. | 73/54.01 |
| 5,269,174 | 12/1993 | Chiba et al. | 73/54.01 |

FOREIGN PATENT DOCUMENTS

| 2192463 | 1/1988 | United Kingdom | 73/54.01 |

OTHER PUBLICATIONS

J. Air Waste Manage. Assoc., vol. 42, No. 10, pp. 1372–1376, Oct. 1992, Laura Staley, "Site Demonstration of the Retech Plasma Centrifugal Furnace: The Use of Plasma to Vitrify Contaminated Soil".

Plasma Centrifugal Furnace Development Program at the CDIF, pp. 1 to 30 and A–1 to A–8, Feb. 1993, Stephan T. Kujawa, et al.

Plasma Applications to Waste Treatment, pp. 1–9, Jan. 16–17, 1991, A.J. Vaill, "Plasma Centifugal Furnace Experiment Progress and Preliminary Test Results".

Proceedings of the International Topical Meeting on Nuclear and Hazardous Waste Management Spectrum '94, pp. 848–855, Aug. 14–18, 1994, D. Battleson, "Latest Developments of Plasma Technology at the CDIF".

*Primary Examiner*—Hezron E. Williams
*Assistant Examiner*—Daniel S. Larkin
*Attorney, Agent, or Firm*—Oblon, Spivak, McClelland, Maier & Neustadt, P.C.

[57] ABSTRACT

A system of determining a viscosity of a melt in a centrifugal furnace. In this system, the centrifugal furnace is rotated at a first rotational speed. The rotational speed of the centrifugal furnace is then changed to a second rotational speed. At least one physical characteristic is then measured during the transition from the first rotational speed to the second rotational speed. Based on this at least one measured physical characteristic, the viscosity of the melt can be determined. This at least one physical characteristic may be a time varying torque required to change the rotational speed of the centrifugal furnace from the first rotational speed to the second rotational speed. This at least one physical characteristic may also be a surface velocity and/or a height of the melt at a predetermined radial position in the centrifugal furnace in comparison with a velocity of the centrifugal furnace at the predetermined radial position. This at least one physical characteristic may also be a time variation of a change in a slope of the melt during the transition from the first rotational speed to the second rotational speed.

16 Claims, 9 Drawing Sheets

CONVENTIONAL PLASMA CENTRIFUGAL FURNACE

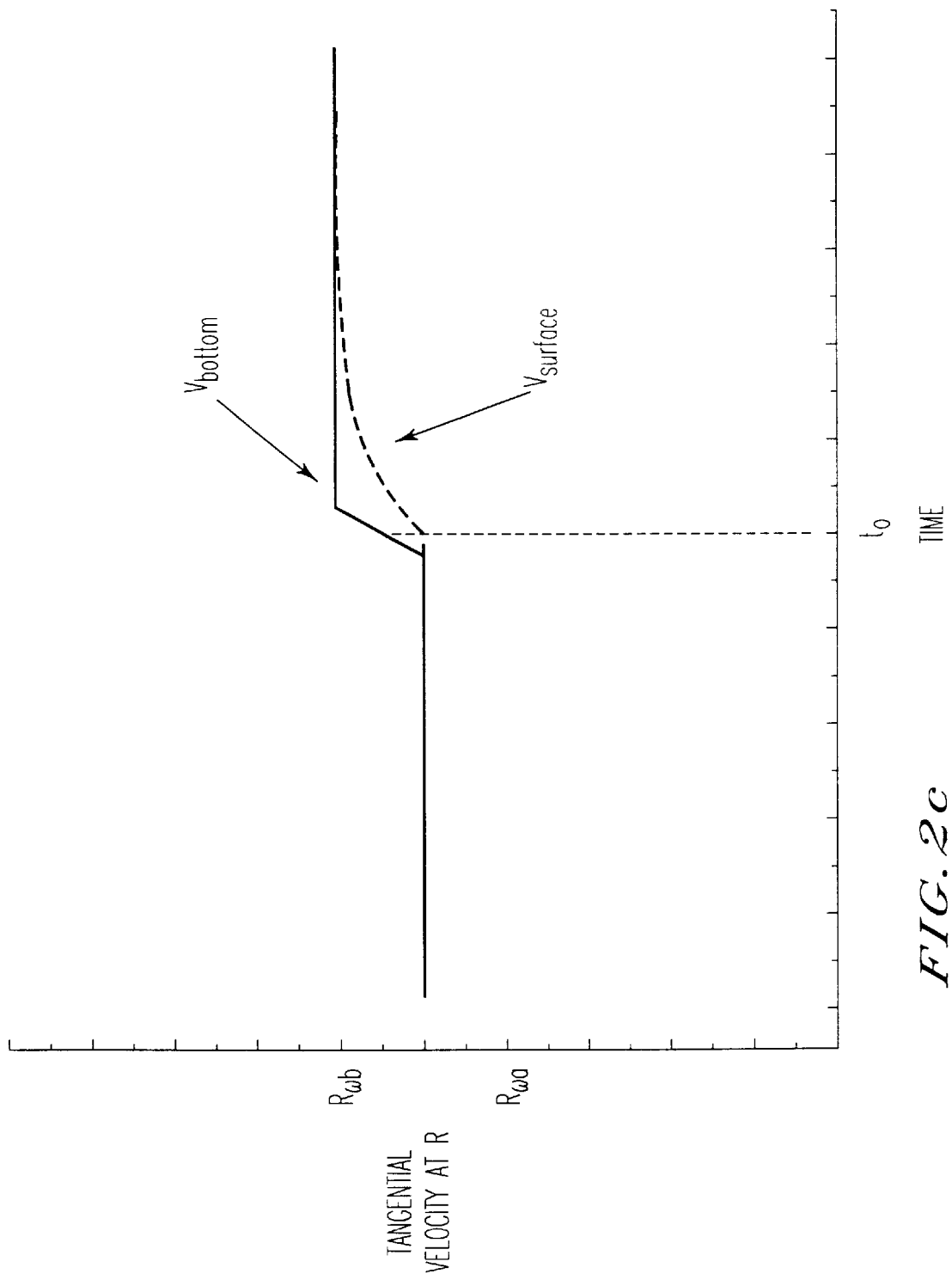

MEASUREMENT OF VISCOSITY OF A MELT IN A PLASMA CENTRIFUGAL FURNACE

BACKGROUND OF THE INVENTION

1. Field of the Invention

The present invention applies to a device which can measure a viscosity of a molten melt in situ and in real time in a plasma centrifugal furnace.

2. Discussion of the Background

The use of a rotating plasma furnace is being considered for the treatment of nuclear and hazardous waste. Countries throughout the world have now amassed enormous stockpiles of hazardous waste which will take many years and many billions of dollars to remediate.

One process of eliminating such hazardous waste which is currently being assessed by at least the U.S. Environmental Protection Agency (E.P.A.) and the Department of Energy (D.O.E.) is the vitrification of such hazardous waste. In such a process, the hazardous waste material is heated to a very high temperature, which thereby drives off any organic volatile components in the waste material. The remaining material is then left as a molten mass, which forms a glassy structure upon cooling. This vitrification process reduces the volume of the waste, allows hazardous and/or flammable solvents to be eliminated, and can trap the radioactive components in the cooled glass structure, in which case it is extremely resistant to leaching and more suitable for long term disposal. The waste types which can possibly be processed by such a vitrification process include transuranic waste (TRU), mixed waste containing both hazardous and radioactive constituents, and ground soil contaminated with heavy metals. Such waste may also include obsolete weapon parts.

A device which is utilized for such a vitrification process may be a plasma centrifugal furnace. Examples of such a device are disclosed in U.S. Pat. Nos. 4,770,109, 5,005,494 and 5,136,137, and in "A Portable Vitrification System for Waste Treatment", presented at AIChE Mixed Waste Conference, Denver Colo., Aug. 14–17, 1994, Eschenbach et al.

FIG. 1 of this paper to Eschenbach et al is reprinted as FIG. 1 here to show the use of such a plasma arc centrifugal treatment device. Such a device includes a centrifuge 30, in which a slag bath 35 (corresponding to the waste material and also referred to as the molten melt) is provided. This slag bath 35 is heated by a plasma torch. The plasma torch includes a water cooled electrode 5, a plasma gas injection device 10 and a nozzle 15. The electrical arc produced by this plasma torch attaches at the location 40 to an inside of the water cooled electrode 10. The current then flows, by means of an arc formed of ionized gases, past the gas injection 10, through the nozzle 15, and attaches at the location 20 on the surface of the slag bath 35.

In such a type of plasma centrifugal treatment device and process of utilization, the waste material is fed into a rotating primary chamber of centrifuge 30 as slag bath 35 after the drum of the furnace is brought up to a steady operating temperature of, for example, approximately 1380 K. The centrifugal force holds the slag bath 35 to the sides of the rotating drum of centrifuge 30, as the plasma arc torch heats the waste materials by arc termination 20 to a high temperature of, as an example, 1920 K, thereby melting the feed materials and driving off the organic volatiles. Off gases are exhausted to a secondary combustion chamber where appropriate conditions are maintained to ensure complete destruction of the organic contaminants. When the processing of the slag bath 35 of the waste is finished, the rotation rate of the drum of the centrifugal furnace is reduced, and the melt, which is now in the form of a molten glass slag 25, exits by gravitational force through a center hole at a bottom of the drum of centrifuge 30 to a slag collection chamber. At this time, this slag melt 25 solidifies into a low volume non-leachable glass structure.

In such a plasma arc centrifugal furnace employing such a vitrification process, it is necessary to determine the viscosity of the slag bath 35 in situ. If the slag bath 35 is too viscous, then the drain hole may plug during the pouring of the slag bath 35 into the slag collection chamber. If the viscosity of the slag bath 35 is too low, then the melt may corrode/dissolve the refractory lining of the furnace. Furthermore, it is believed that the viscosity of the molten slag bath 35 has a correlation to the quality of the final glass structure. Thus, determining the viscosity of the slag bath 35, before the rotation rate of the drum of the centrifuge 30 is decreased to discharge the slag bath 35 through the drain hole, can provide a useful means to control the final glass structure.

The viscosity of the molten slag bath 35 can be controlled by several methods, depending on the particular process situation. One can control the slag bath 35 viscosity by adjusting the melt temperature (through the amount of heat addition and/or the duration of the heating process) or by varying its composition (through the addition of additives to the slag bath 35). In either case, a quick and reliable method of determining the slag bath 35 viscosity in real time is required, while one adjusts the process variables.

It has been known to measure a viscosity of a liquid by enclosing a liquid between two cylinders (or two disks). In such devices, by keeping one cylinder fixed while the other cylinder is rotated, the viscosity of the liquid can be deduced from a measured torque on either cylinder. Similarly, a rotating bob, stirrer, or paddle wheel can be placed in a stationary container of liquid and the torque required to rotate the bob, etc. can be measured.

However, for the purpose of measuring the viscosity of molten radioactive waste, these known devices suffer from the disadvantage of requiring a portion of the molten melt to be extracted from the treatment system and placed in a separate device for measuring viscosity. Furthermore, the temperature of the measurement device must be maintained at the same temperature as the molten melt (because the viscosity is a strong function of the temperature, and the molten melt will solidify if it cools too much).

Moreover, these methods, and many possible variations upon them, are all based upon a common principle. This principle is that the rotational motion is in a steady state and that the torque required to maintain the rotational motion is also in a steady state, i.e. not varying as a function of time. Further, in these methods the shearing motion necessary to measure the viscosity is set up between one member which rotates and another member which is stationary.

SUMMARY OF THE INVENTION

Accordingly, one object of the present invention is to provide a novel system for determining the viscosity of a molten melt in situ in a rotating centrifugal furnace, and allowing an operator to change a process chemistry or processing time to bring the melt viscosity into a desired range.

The system of the present invention may find particular application in determining the viscosity of a molten melt which contains nuclear and/or hazardous waste materials which are subject to a vitrification process in a plasma centrifugal furnace.

The present invention achieves such objects in a system in which the centrifugal furnace is rotated at a first rotational speed. The rotational speed of the centrifugal furnace is then adjusted to a second rotational speed. Moreover, at least one physical characteristic is then measured during the transition from the first rotational speed to the second rotational speed, and by appropriately determining the at least one physical characteristic, the viscosity of the molten melt can be calculated from the at least one measured physical characteristic.

As one feature, the system of the present invention can measure a torque required to change the rotational speed of the centrifugal furnace from the first rotational speed to the second rotational speed. In this system, the viscosity of the molten melt can be determined from the time required to change the rotational speed of the centrifugal furnace from the first rotational speed to the second rotational speed.

As a further feature of the present invention, at least one physical property which is measured may be a surface velocity of the molten melt at a predetermined radial position in the centrifugal furnace. Then, the viscosity of the molten melt can be determined from a time required for the measured surface velocity to equal the rotational speed of the drum of the centrifugal furnace at the predetermined radial position.

In this feature of the present invention, the viscosity can also be ascertained by determining a ratio of the tangential velocity of the molten melt at the predetermined radial position relative to the velocity of the drum of the centrifugal furnace at the same predetermined radial position.

As a further feature of the present invention, the physical property which is measured may be the height of the molten melt within the centrifugal furnace. In this operation, the viscosity of the molten melt can be determined by evaluating the time required for the molten melt height to vary, and the amount of variation in the molten melt height, during the transition from the first rotational speed to the second rotational speed.

As a further feature of the present invention, the physical property which is measured may be a time variation of a change in slope of the molten melt surface during the transition from the first rotational speed to the second rotational speed.

The system of the present invention provides the significant advantages of being able to accurately and easily make a determination of the viscosity of a molten melt in a plasma centrifugal furnace. Further, the system of the present invention allows such a determination of viscosity to be made in situ. This provides a significant advantage in the present invention that if the molten melt includes toxic, radioactive or hazardous materials, a sample of the molten melt does not have to be extracted from the plasma centrifugal furnace.

Furthermore, the system of the present invention provides the advantages that the determination of viscosity is at the actual temperature of the molten melt and is performed prior to the molten melt being discharged, to thereby provide a method which allows an operator to adjust the process to bring the melt viscosity within a desired range and to provide a highly accurate control of when the plasma centrifugal furnace rotation should be reduced for discharging the melt.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 2(c) shows a change in a tangential velocity of a melt in a plasma centrifugal furnace as in the present invention;

DESCRIPTION OF THE PREFERRED EMBODIMENTS

Figure 1:
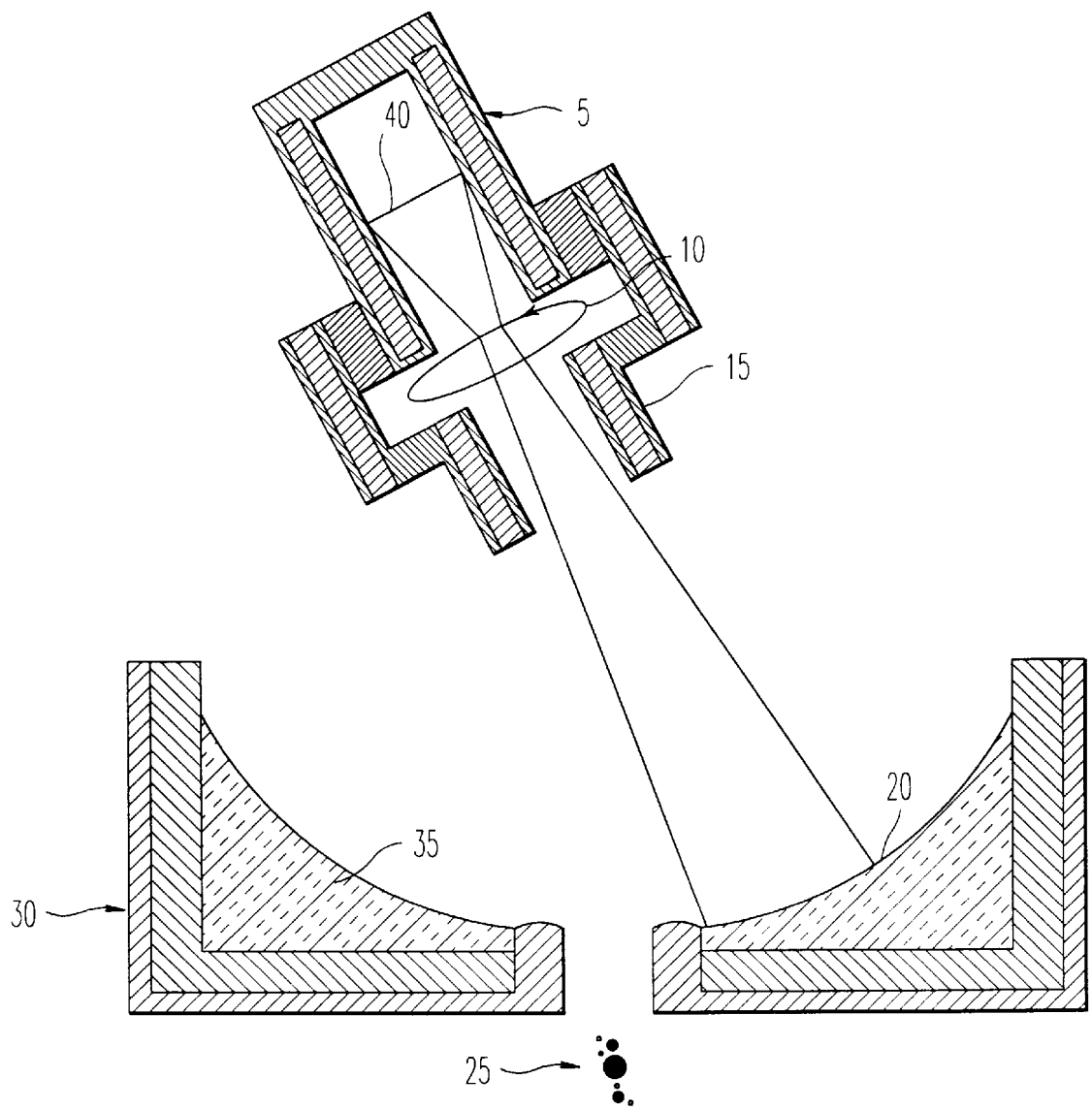
FIG. 1 shows a plasma centrifugal arc furnace to which the present invention can be applied.

Referring now to the drawings, wherein like reference numerals designate identical or corresponding parts throughout the several views, the subject matter of the present invention will now be described in greater detail.

Figure 5:
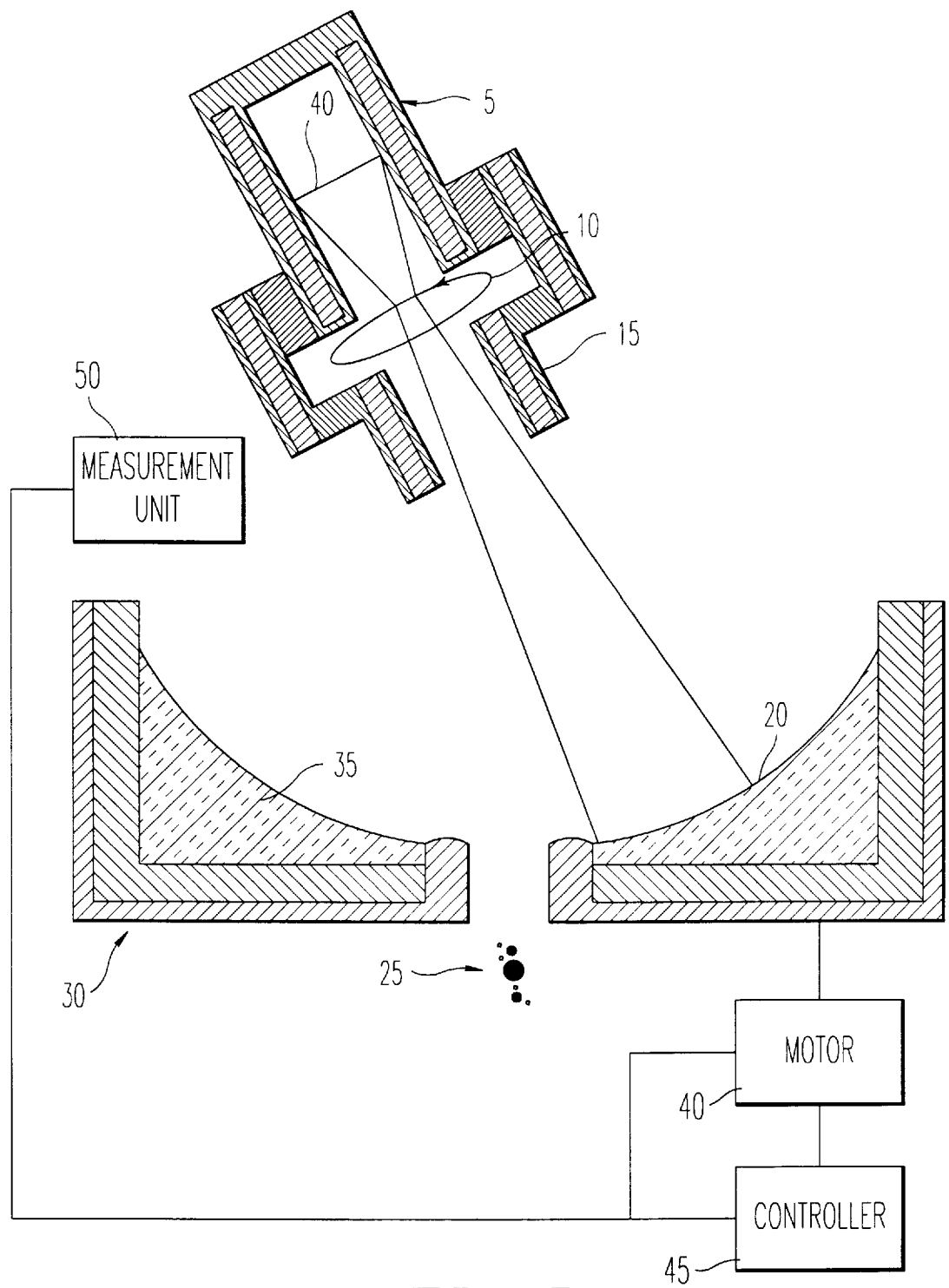
FIG. 5 shows a centrifugal furnace of an embodiment of the present invention.

The system of the present invention can operate in a standard plasma centrifugal furnace, such as is shown in FIG. 5, which is similar to the embodiment shown in FIG. 1, except a motor 40 for controlling rotation of the centrifuge 30 is shown, and a controller 45 to control the operation of the motor 40 and to receive measurement signals from a measurement unit 50 are provided. The system of the present invention can be applied to other plasma centrifugal furnaces. As discussed above, such a plasma centrifugal furnace can be utilized for the vitrification of waste materials. The present invention provides a system which can also be easily retrofitted on such an existing plasma centrifugal furnace to determine a viscosity of a molten melt contained inside the plasma centrifugal furnace.

The system of the present invention can also be applied to the measurement of viscosity in other rotating devices, and is not necessarily limited to plasma centrifugal furnaces or devices for the processing of hazardous wastes.

The inventors of the present invention have recognized that one way to measure a viscosity of a molten melt in such a plasma centrifugal furnace is to use properties of the molten melt itself, since such a molten melt is already contained in the plasma centrifugal furnace. Such an operation of the present invention is conceptually similar to determining a characteristic response time of a system, similar to determining a "time constant" in a simple electronic circuit composed of a resistor and a capacitor. In such an operation, a known input is provided into a system, and a system output is then measured, so that the "transfer function" of the system can be determined.

The inventors of the present invention have recognized that the viscosity of a molten melt in a plasma centrifugal furnace can be measured in such a way by measuring a relationship between an input (for example change in drum rpm of the plasma centrifugal furnace) and the output (for example change in fluid rpm) of a system. Such a molten melt does not respond immediately to a change in drum rpm; i.e. there is a time lag. A transfer of rotation from the drum to the molten melt occurs through the action of fluid viscosity. Therefore, a more viscous fluid responds more rapidly than a less viscous fluid. The inventors of the present invention have recognized this and set forth a system to measure or quantify such a time lag, from which the viscosity of the molten melt can be determined.

Three measurement operations are contemplated according to the present invention. All three operations are variations on the same basic principle. Namely, when the rotating velocity of the drum of the centrifugal furnace is changed suddenly, the molten melt inside the drum tries to adjust to the change. In the present invention, the melt viscosity is determined from the various measured characteristics of the molten melt during this period of readjustment. The different operations have distinct advantages depending on the furnace arrangement, vat size, and melt properties.

In each of the measurement operations of the present invention, the drum of the centrifugal furnace is initially rotating at a constant rotational frequency $\omega_a$. The rotation of the drum is then adjusted quickly to $\omega_b$, where the value of $\omega_b$ is higher or lower than $\omega_a$, for example 10–20 percent, or other values, higher or lower than $\omega_a$.

In a first measurement operation of the present invention, the torque required to accelerate or decelerate the drum of the centrifugal furnace, i.e. change the drum rpm, its refractory lining and any glass frozen to the sides of the refractory is considered. This portion of the torque required for the acceleration or deceleration is independent of the molten melt viscosity. However, an additional torque is required to accelerate or decelerate the molten melt inside the drum. For a viscous melt, the melt responds quickly to the change in drum rpm, and thus the additional torque required to produce a change in the molten melt corresponding to the change in the drum rpm occurs soon after the change in drum rpm. On the other hand, a less viscous melt responds more slowly to the change in drum rpm. This means that the additional torque required to change the molten melt corresponding to the change in the drum rpm is spread out over a longer time interval.

In this first measurement operation, the magnitude of the melt viscosity is inferred from the measured time-varying torque required to produce a given change in the outer drum rpm (i.e., from $\omega_a$ to $\omega_b$). This measurement is obtained by controller 45 receiving feedback signals from motor 40.

Alternatively, a specified torque could be applied to the system, and the resultant time-varying rpm could be measured, from which the melt viscosity can be determined.

Figure 4:
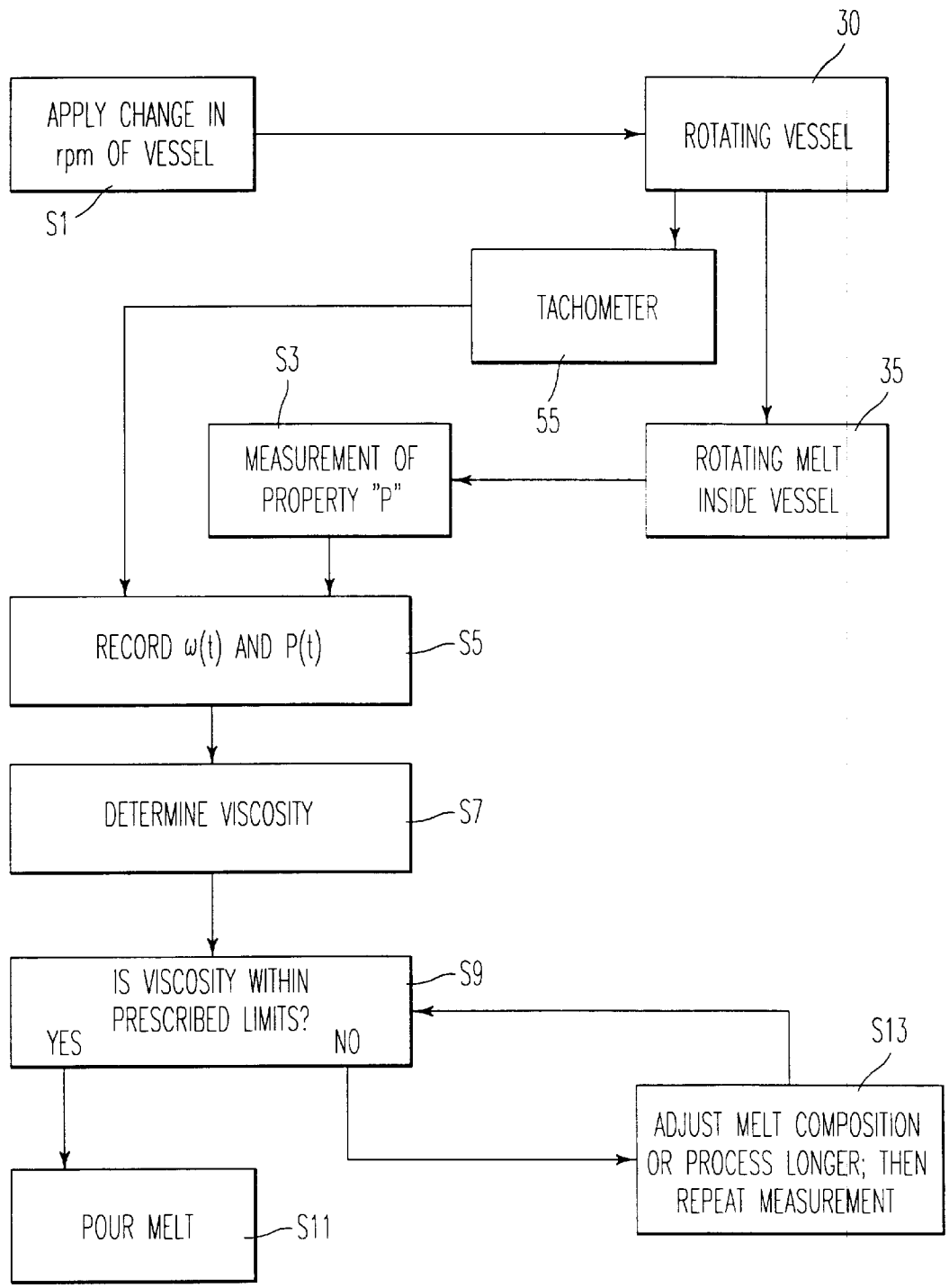
FIG. 4 shows a measurement control operation according to one feature of the present invention.

FIG. 4 shows an outline of the control operation of the present invention. The elements to the right hand side of the dotted line in FIG. 4 represent elements of the plasma centrifugal furnace, and the control steps to control such a plasma centrifugal furnace to achieve the operation of the present invention are shown on the left hand side of the dotted line in FIG. 4.

In the operation of the present invention, the rotating vessel 30 of the plasma centrifugal furnace will initially be rotating at a steady state, and then in a step S1 the rotational speed of the rotating vessel or centrifuge 30 of the plasma centrifugal furnace is changed. For example, and as discussed above, the rotational speed of the rotating vessel 30 may be increased or decreased by 10–20%, as examples only. In this operation of the present invention, a tachometer 55 is connected to the rotating vessel 30 to measure the rpms of the rotating vessel 30. This tachometer 55 may form an element of the measurement unit 50 shown in FIG. 5 of the present specification.

The molten melt 35 inside the vessel also has a property "P" being measured, see step S3. As discussed above, the change in the rotational speed of the rotating vessel 30 causes changes to the rotating molten melt 35, although such changes do not occur immediately but have a lag time which is indicative of the viscosity of the molten melt 35.

In step S3, as noted above, a property "P" of the molten melt 35 is measured. This property "P" may be some characteristic of the molten melt 35 which can be measured and which undergoes a change as the molten melt 35 changes from one rpm to another. As discussed above, and as is discussed further below, this property "P" could be, for example, (1) the torque on the rotating vessel 30, (2) the surface velocity of the molten melt 35 at a specific radius (3c), (3) a height of the molten melt 35 at a particular radius, which can further include (3a) a diameter of a dry circle in the molten melt 35 in the bottom of the rotating vessel 30, and/or (3b) a height of the molten melt 35 on the sides of the rotating vessel 30, and (4) a slope of a surface of the molten melt 35.

In step S5, the rotational speed of the rotating vessel 30 and the measured property "P" of the molten melt 35 are recorded as a function of time, $\omega(t)$ and $P(t)$ respectively. The present invention may record the time varying (transient) quantities of the rpm of the vessel $\omega(t)$ and the response $P(t)$ of the molten melt 35 inside the rotating vessel 30 during the time interval during which the vessel is changing rpm and the molten melt 35 inside the rotating vessel 30 is adjusting to this change in rpm. Both of these measurements $\omega(t)$ and $P(t)$ are signals which vary as a function of times and may either be recorded continuously, or a succession of measurements may be made at predetermined intervals.

Then, in the present invention the viscosity of the molten melt 35 is determined in step S7 based on the recorded values in step S5. As discussed above, if there is a long time lag between the applied change in rpm of the rotating vessel 30 and the response of the molten melt 35, as indicated by the measured property $P(t)$, the molten melt 35 has a small viscosity. If the response of the molten melt 35 is more immediate, then the viscosity of the molten melt 35 is greater. This step S7 may also require input of certain information about the amount of molten melt 35 in the rotating vessel 30. The precise algorithms used to perform such a determination are discussed below.

In step S9 it is then determined whether the viscosity of the molten melt 35 is within prescribed limits. As an example, it may be desirable for the molten melt 35 to have a viscosity between 20–100 poise.

If the viscosity of the molten melt 35 is acceptable, i.e., YES in step S9, the molten melt 35 is then poured in step S11. If the viscosity of the molten melt 35 is not acceptable, i.e., NO in step S9, the system proceeds to step S13 in which steps can be taken to change the viscosity of the molten melt 35 until it is acceptable. For example, a feed composition could be altered, to create a molten glass mixture with different properties, additives could be added to the molten melt 35 to adjust its viscosity, or the molten melt 35 could be processed longer and/or heated to a higher temperature, to thus lower the viscosity thereof. After step S13, the measurement process of the molten melt 35 can then be repeated until the molten melt 35 is determined to have an acceptable viscosity.

In the case as discussed above with reference to FIG. 4, it is required to accelerate or decelerate the drum of the centrifugal furnace within a time span short compared to the time required for the melt inside the drum to respond. However, this operation is more difficult if the mass of the melt is small compared to the mass of the drum. The accuracy of this method also increases with increasing sizes of the waste load.

A second variation of the present invention involves measuring by measurement unit 50 the surface velocity of the molten melt within the drum of the centrifugal furnace. There at least two possible methods by which the surface velocity of the molten glass could be measured. First, if the molten glass surface contains air bubbles or other distinguishable surface features, tracking these features with a video camera would allow determination of how fast these features, and thus the glass, was moving. A second possibility would be to use an existing technology, available commercially from TSI, Inc., to measure the surface velocity of the glass using scattered laser light.

Figure 2A:
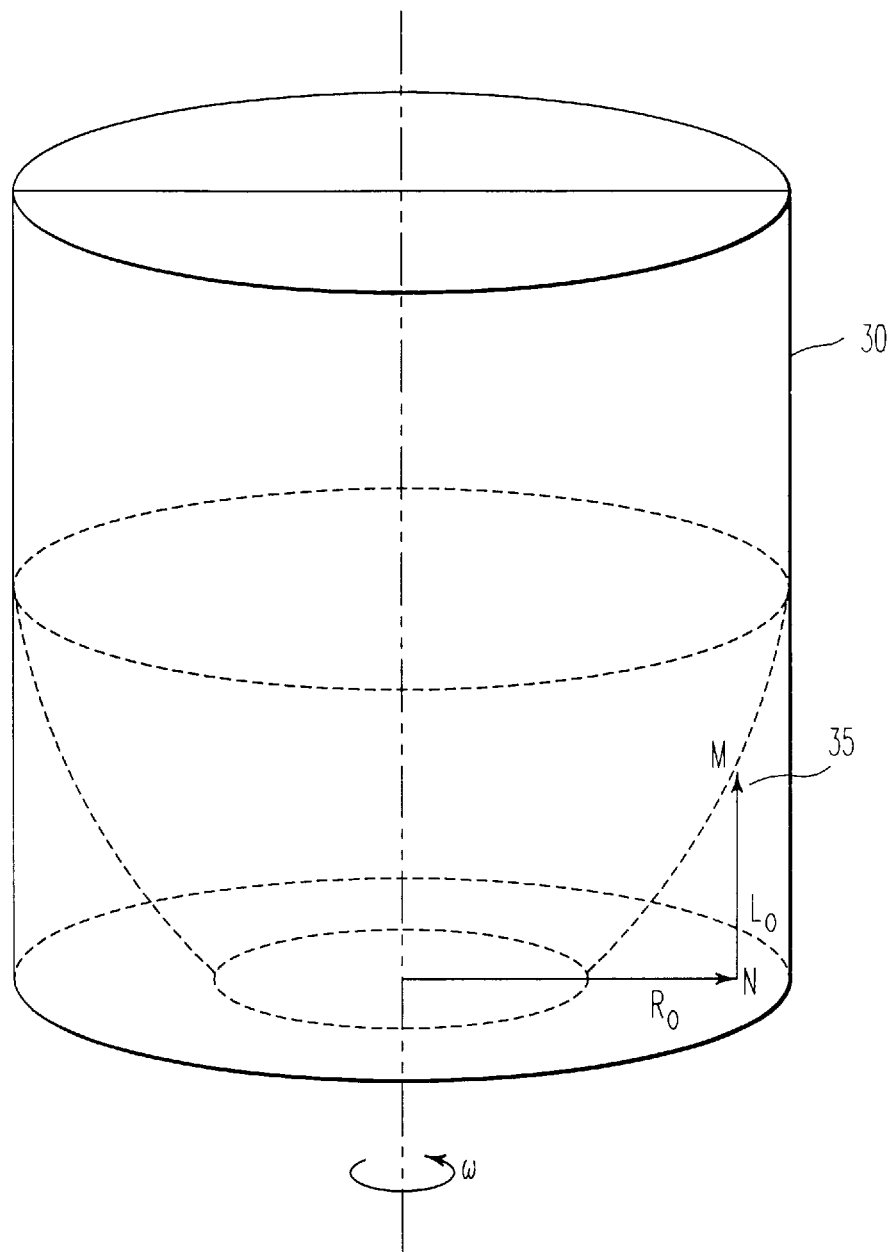
FIG. 2(a) shows dimensions of a molten melt within a drum of the plasma centrifugal furnace.

As shown in FIG. 2(a), a molten melt 35 within a drum of a centrifuge 30 has a surface which is saucer shaped as the drum of the centrifugal furnace is rotating. In the present invention, at point M on a surface of the molten melt 35, which is a radial distance $R_0$ from the center of the drum, the tangential velocity of the melt is defined as $V_{surface}$. The tangential velocity of the drum at this same radial distance $R_0$, point N in FIG. 2(a), is defined as $V_{bottom}$. As a result, the molten melt height $L_0$ is the straight line connecting points M and N.

For a solid body rotating at some angular velocity $\omega$ about a fixed axis of rotation, it is well known that the velocity of any point in this body is perpendicular to the line connecting that point to the axis of rotation (i.e., the velocity vector is in the "tangential" direction in an (r, θ, z) cylindrical coordinate system, referring to the velocity component in the θ direction). Furthermore, if $R_0$ is the distance from that point to the axis of rotation, then the magnitude of this tangential velocity is $R_0\omega$.

Thus, if the rotating drum is accelerated or decelerated from a first angular velocity $\omega_a$ to a second angular velocity $\omega_b$ at a certain time, $t_0$, then the tangential velocity of the bottom of the drum, being part of a solid body, increases from $R_0\omega_a$ to $R_0\omega_b$ at $t_0$.

Assume that an existing commercially available method is employed for measuring the velocity of the molten melt 35 by measuring unit 50 directly above this point on the bottom of the drum, at the same chosen radial distance $R_0$. Then, at the start and at the finish of this change in angular velocity, the change in angular velocity of the molten melt is the same as if it were a rotating solid body. Thus, the velocity of the molten melt is $R_0\omega_a$ at $t_0$, and eventually reaches a final value of $R_0\omega_b$. In the interim, however, the motion of the molten melt lags behind the motion of the bottom of the drum, and thus $V_{surface}/V_{bottom}$ has a value between zero and one; $V_{surface}/V_{bottom}$ has an initial value of $\omega_a/\omega_b$ at $t_0$, and increases asymptotically to a final value of one.

The inventors of the present invention have recognized that the time required for this transition contains information about the viscosity of the molten melt.

Figure 2B:
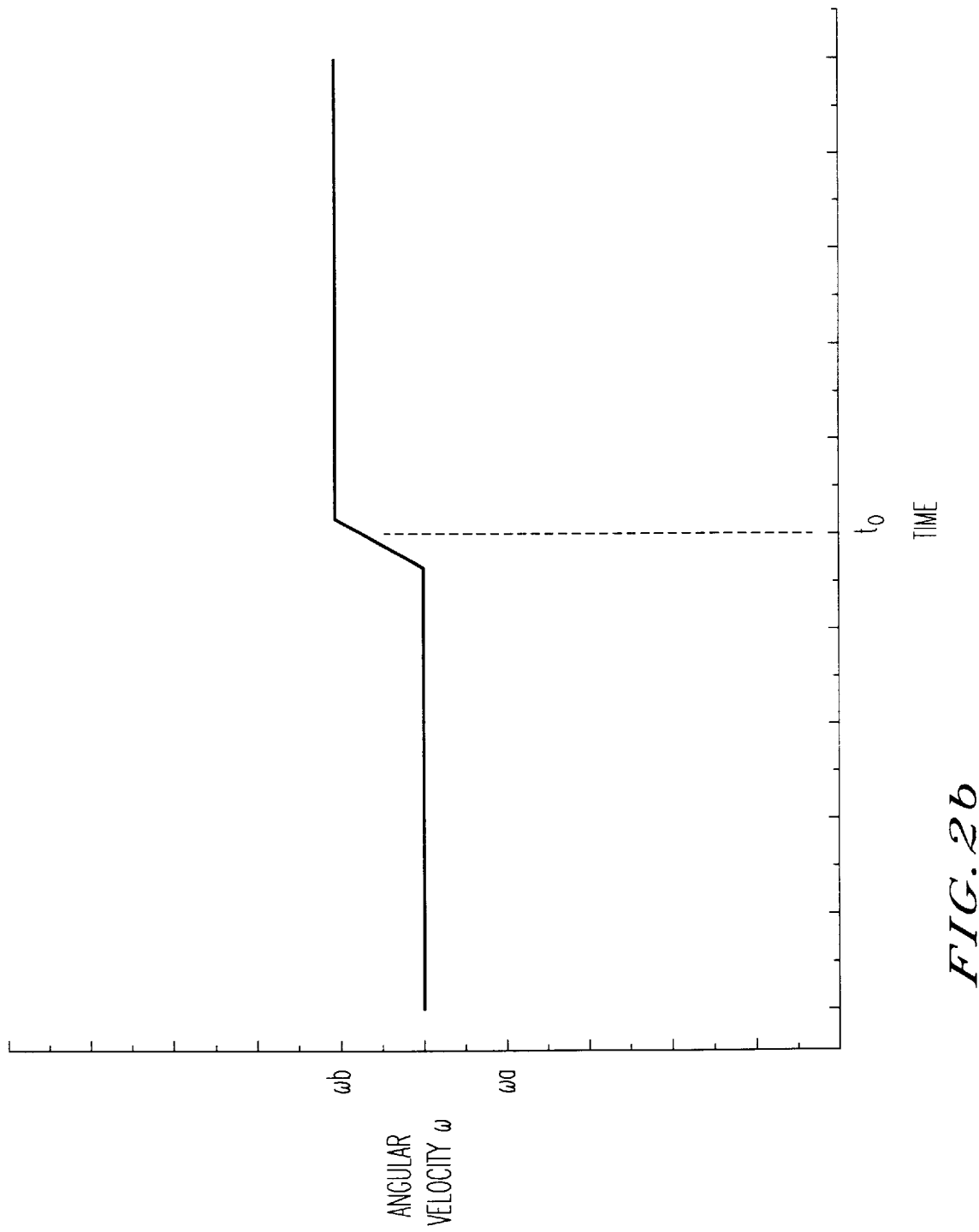
FIG. 2(b) shows a change in rotational speed of the drum of the plasma centrifugal furnace of the present invention.

A second variation of the present invention is now discussed with reference to FIG. 2(b). As shown in FIG. 2(b), the drum of the centrifugal furnace is initially rotating at a constant frequency $\omega_a$. At time $t_0$, the drum rotation is adjusted quickly to $\omega_b$, where the value of $\omega_b$ is higher than $\omega_a$ as shown in FIG. 2(b), for example in the range of 10–20 percent higher than $\omega_a$; although $\omega_b$ could also be approximately 10–20 percent lower than $\omega_a$. During this time, the tangential surface velocity ($V_{surface}$) at point M of the molten melt at the particular radial location ($R_0$) is monitored and recorded. The variation in $V_{surface}$ is shown in FIG. 2(c), as well as that of $V_{bottom}$, equals ($R_0\omega$) of the drum of the centrifugal furnace. The length of time $\Delta t$ required for $V_{surface}$ to readjust to ($R_0\omega$) is related to the melt viscosity and to the melt height, $L_0$. Hence, knowing $\Delta t$ from FIG. 2(c) and the value of $L_0$, the melt viscosity can be determined.

Based on dimension analysis, for a container with a characteristic dimension "L", rotating at an angular velocity "$\omega$", and containing a liquid with a kinematic viscosity "v", the characteristic spin-up time $t_{char}$ scales according to:

$$t_{char} = \sqrt{\sqrt{L^2/\omega v}}$$

A numerical solution, similar to the ones described in: H. Goller and T. Ranov, "Unsteady rotating flow in a cylinder with a free surface", Transactions of the ASME, Journal of Basic Engineering, December 1968, pp. 445–454; and G. F. Homicz and N. Gerber, "Numerical model for fluid spin-up from rest in a partially filled cylinder", Transactions of the ASME, Journal of Fluids Engineering, Volume 109, June, 1987, pp. 194–197; may be used to relate the observed readjustment time of the molten melt to its viscosity.

There are also several methods that might be used for data analysis, that is, the operation of determining the viscosity of the molten melt from the measurements.

For one, a numerical model of the spin-up process, similar to those described in the papers listed above, could be used to compute a value of the surface height, or surface velocity of the molten melt, or the torque required, and these calculated values can be compared to actual measurements. Then, in a case of non-agreement, the value of the molten melt viscosity used as an input into the numerical model could be adjusted until the model predictions match the actual measurements.

As an alternative, consider the variation $V_{surface}$ described previously. When the drum is accelerated from an angular velocity of $\omega_a$ to $\omega_b$, the molten melt velocity at a chosen radius $R_0$ changes from $R_0\omega_a$ to $R_0\omega_b$. It is not possible to unambiguously determine the time required for this transition, because the molten melt velocity asymptotically approaches its final value. But, as an example, the time required for the molten melt velocity to reach a certain fraction of its final value can be taken as the time required for the spin-up process. If 50%, for example, were the fraction chosen, then the data can be examined and the time elapsed from $t_0$ until the time when the fluid velocity reaches $R_0\omega_a + 0.5(R_0\omega_b - R_0\omega_a)$ could be determined, which corresponds to the time the required for the molten melt to achieve half of its ultimate velocity change from $R_0\omega_a$ to $R_0\omega_b$.

Values of the characteristic response time, determined in this way, could be compared to values previously determined by numerical models or experiment, and related to the fluid viscosity.

The current state of the art in signal processing contains many other methods and calculational algorithms which could be employed to identify the time lag between two sets of measurements, which also applies to the other fluid response variables which might be measured, such as the free surface height, or the torque.

To illustrate how the value of Δt is influenced by the viscosity of the melt within the drum, one can consider the two limiting cases of an inviscid melt and an infinitely viscous melt. If the melt is inviscid, then the value of Δt would be infinite; the melt surface would never adjust to $\omega_b$ because of the slip interface at the wall surface of the drum. For the infinitely viscous melt, ←t equals zero; this is because the liquid and the drum rotate as a solid body and the rotational adjustment at the liquid surface is instantaneous.

Alternatively, measurements by measurement unit 50 of variations in melt height $L_0$ during the period of rotational adjustment of the drum may be another approach to infer values for the viscosity.

The essential idea here is to change the rpm of the plasma arc centrifugal furnace drum containing the molten melt and observe the response of the molten melt. The time required for the molten melt to adjust to the new rotational speed is measured.

One attribute of the molten melt which changes when the drum adjusts from one rpm $\omega_a$ to another $\omega_b$ is that the shape of the liquid surface changes. If the drum is rotating at a fixed rpm, then the molten melt surface inside has a parabolic shape. If, for example, the drum rpm is increased, then the parabolic molten melt surface changes, and becomes steeper, but is still a parabola.

Thus, at certain radii, the molten melt depth will increase and at others it will decrease. There are existing technologies that could possibly be employed to measure this property. For example, there are methods for non-contact measurement of distances, such as laser based methods of measuring distances by the elapsed time required for a laser pulse travel to the surface and back. Acoustic variations on the same technique are also possible. One could also measure the depth of the liquid at a certain radius by measuring the attenuation of radiation as it passes through the liquid.

Another alternative is to measure, instead of the molten melt height at some arbitrary radius, the points where the molten melt surface intercepts an inner surface, e.g. the bottom and the side walls, of the cylindrical drum which contains the molten melt. As the steepness of the parabola changes, the locations of these intercepts changes.

For example, an intersection of the parabolic (actually, a paraboloid of revolution) molten melt surface with the bottom of the drum defines a circle, of some definite diameter, which separates the area of the drum bottom which is covered by the molten melt from that which is uncovered. As the molten melt adjusts to the new, higher rpm, this dry circle diameter increases. Likewise, the height which the molten melt reaches on the side walls of the drum increases as the molten melt "spins up".

Either or both of these distances could be measured by measurement unit 50. For example, the spin up process could be recorded with a video camera, and the diameter of the dry circle on the bottom of the drum as a function of time could be determined from the video images. The same applies to the height the liquid reaches on the side walls.

These measurements would then be related to the viscosity by means of calculations or experimental calibration, as discussed previously.

A further operation of the present invention also evaluates the tangential velocity at a surface of the molten melt related to a tangential velocity of the drum at the same radial positions.

Figure 3A:
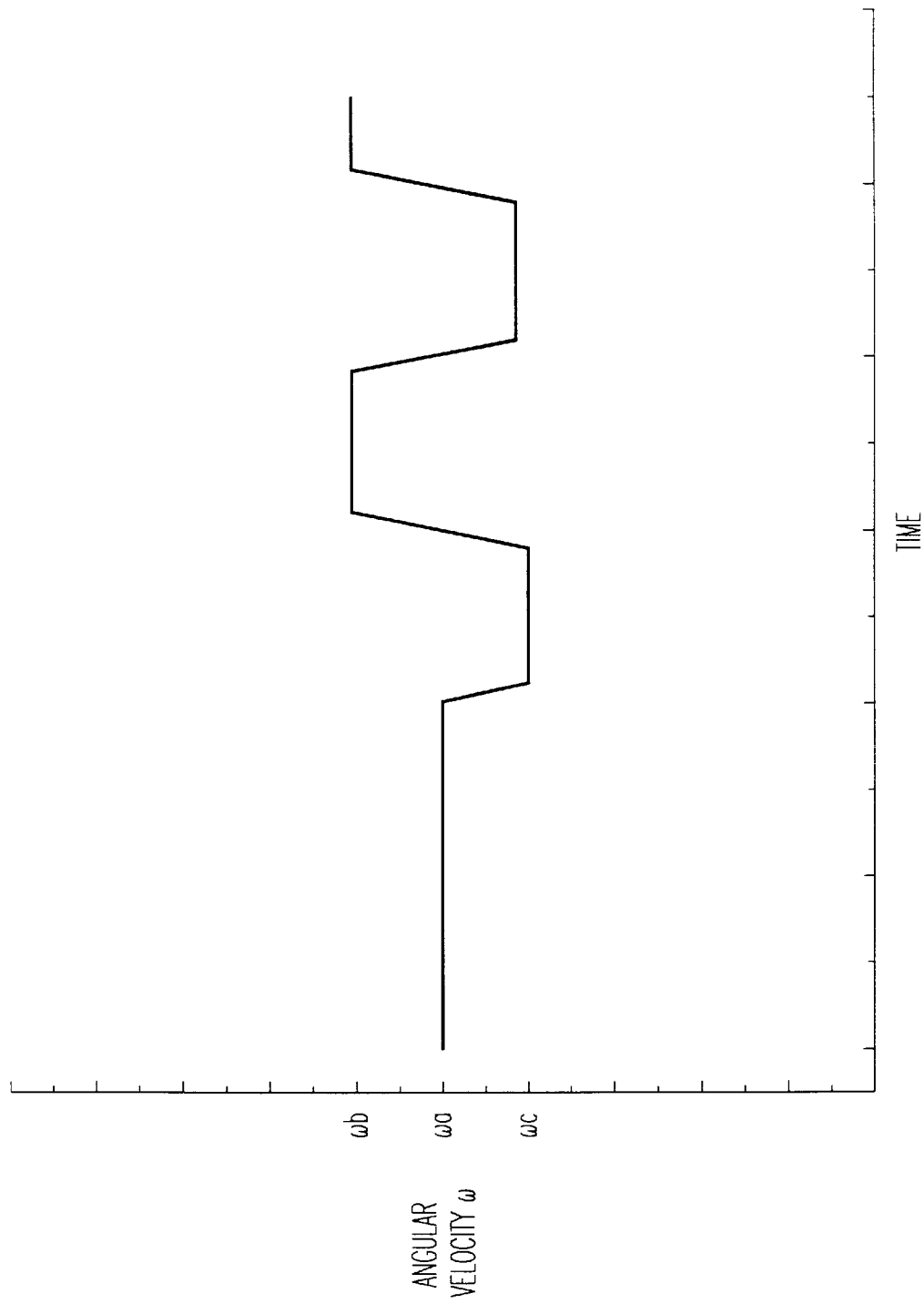
FIG. 3(a) shows a further change in a rotational velocity of a drum of a plasma centrifugal furnace as in the present invention.
Figure 3B:
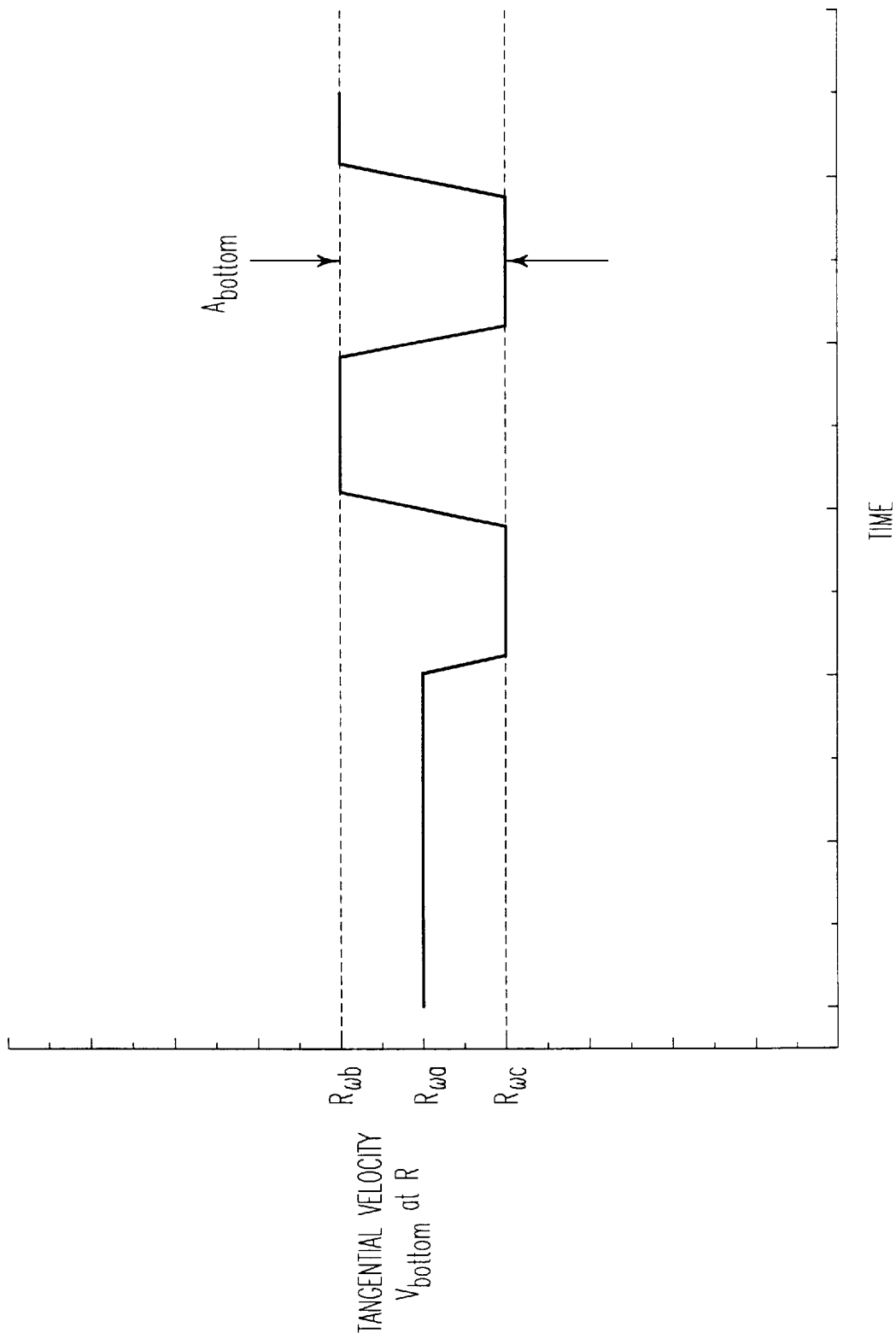
FIG. 3(b) shows a measurement of a velocity of a predetermined radial position of the drum of the plasma centrifugal furnace according to the present invention.

In this operation, the drum is initially rotating at constant frequency $\omega_a$. Whenever a melt viscosity measurement is desired, the rotation speed of the drum is adjusted by motor 40 under control of controller 45 in a cyclic fashion, as shown in FIG. 3(a), where $\omega_b$ and $\omega_c$ have values that are 10 percent higher and lower than $\omega_a$, respectively. Again, the velocity of the molten melt surface, $V_{surface}$, at a particular radial position M of the drum, $R_0$, is monitored throughout the period of rotational adjustments. Time variations of measured $V_{surface}$ and $V_{bottom}$ can be compared as in FIG. 3(b). The viscosity of the molten melt can be determined knowing the value of the ratio $A_{surface}/A_{bottom}$ and the melt height $L_0$, see FIG. 3 for the definition of $A_{surface}$ and $A_{bottom}$. The characteristic time period of the cyclic change in $\omega$ should be of the order of Δt.

Figure 3C:
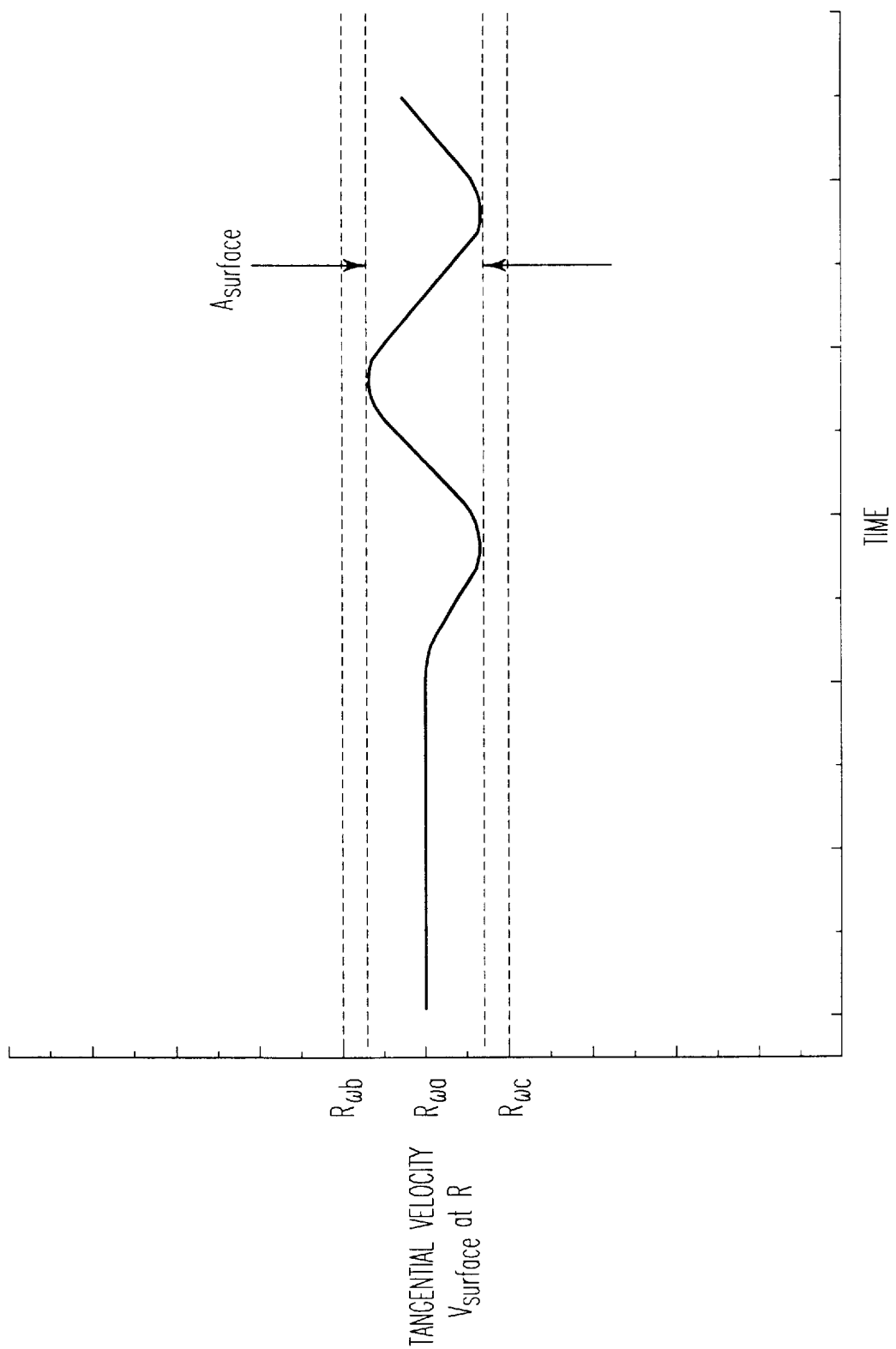
FIG. 3(c) shows a measurement of a tangential velocity of a surface of the melt at the predetermined radial position in the plasma centrifugal furnace as in the present invention.

As shown in FIG. 3, the idea here is to excite a system with a periodic signal. In this case, the excitation is a periodic variation in the drum rpm. For example, at a certain radius $R_0$, cyclically varying the rpm of the drum from a maximum value of $\omega_b$ to a minimum value of $\omega_c$ causes the velocity of the bottom of the drum at that location to vary from $R_0\omega_b$ to $R_0\omega_c$.

Due to the inability of the molten melt in the drum to respond immediately to changes in drum rpm, depending on the frequency of this cyclical variation, the tangential velocity of the molten melt at that location $R_0$, as measured at the surface, does not vary as much as the drum velocity at the bottom of the liquid is varying. Here, the ratio of the response amplitude to the excitation amplitude can be taken, as is commonly done to define a frequency response of a system.

In the embodiments discussed above, it is noted that the rotational speed of the drum is changed from a first rotational speed to a second rotational speed. It is noted that this rotational speed can be implemented by either a stepped increase or decrease in the drum rpm, a ramp change in the drum rpm or by utilizing an oscillating drum rpm. Other methods of changing the rpm of the drum can also be implemented.

As a further variation of the present invention, the inventors of the present application have recognized that a slope of the molten melt surface changes as it responds to a change in drum rpm. One alternative method of determining the viscosity of the molten melt is to aim a laser beam which may be included in measurement unit 50 at the surface of the molten melt as the rpms of the drum are changed from the first value $\omega_a$ to $\omega_b$. In such a situation, the reflected laser beam would vary in direction as the molten melt surface changed its slope as a result of the change in drum rpm from $\omega_a$ to $\omega_b$. In this way, the time required for the molten melt surface slope to adjust to the change in the drum rpm could be measured by shining the laser beam from measurement unit 50 at the molten melt surface at a known angle, and by measuring the angle at which the laser beam is reflected. Alternatively, the angle of incidence of the laser beam could be adjusted such that the reflected beam is reflected in a certain direction, as ascertained by a photodetector. In this situation, the amount of adjustment needed until the reflected beam is reflected in the certain direction provides an indication as to the change in slope of the surface of the molten melt.

Obviously, numerous additional modifications and variations of the present invention are possible in light of the above teachings. It is therefore to be understood that within the scope of the appended claims, the present invention may be practiced otherwise than as specifically described herein.

What is claimed as new and is desired to be secured by Letters Patent of the United States is:

1. A method of determining viscosity of a melt in a centrifugal furnace, comprising the steps of:

rotating the centrifugal furnace at a first rotational speed;

changing the rotational speed of the centrifugal furnace to a second rotational speed;

measuring at least one physical characteristic during a transition from the first rotational speed to the second rotational speed; and determining the viscosity of the melt from the at least one measured physical characteristic.

2. The method according to claim 1, wherein the second rotational speed is ten percent greater than the first rotational speed.

3. The method according to claim 1, wherein the second rotational speed is ten percent less than the first rotational speed.

4. The method according to claim 1, wherein the at least one measured physical characteristic is a torque required to change the rotational speed of the centrifugal furnace from the first rotational speed to the second rotational speed, and the step of determining the viscosity ascertains the viscosity from a time varying of the torque required to change the rotational speed of the centrifugal furnace from the first rotational speed to the second rotational speed.

5. The method according to claim 1, wherein the at least one measured physical characteristic is a surface velocity of the melt at a predetermined radial position in the centrifugal furnace, and the step of determining the viscosity ascertains the viscosity from a time required for the surface velocity to equal the rotational velocity of the centrifugal furnace at the predetermined radial position.

6. The method according to claim 1, wherein the at least one measured physical characteristic is a slope of a surface of the melt in the centrifugal furnace, and the step of determining the viscosity ascertains a time variation of the slope in the molten melt during the transition from the first rotational speed to the second rotational speed.

7. The method according to claim 1, wherein the at least one measured physical characteristic is a surface height of the melt, and the step of determining the viscosity ascertains the viscosity from a change in height of the molten melt during the transition from the first rotational speed to the second rotational speed.

8. The method according to claim 1, wherein the at least one measured physical characteristic is a diameter of a dry circle, and the step of determining the velocity ascertains the viscosity from a change in the diameter of a dry circle in the molten melt in the bottom of the rotating vessel during the transition from the first rotational speed to the second rotational speed.

9. A system for determining a viscosity of a melt in a centrifugal furnace comprising:

means for rotating the centrifugal furnace at a first rotational speed;

means for changing the rotational speed of the centrifugal furnace to a second rotational speed;

means for measuring at least one physical characteristic during a transition from the first rotational speed to the second rotational speed; and means for determining the viscosity of the melt from the at least one measured physical characteristic.

10. The system according to claim 9, wherein the second rotational speed is ten percent greater than the first rotational speed.

11. The system according to claim 9, wherein the second rotational speed is ten percent less than the first rotational speed.

12. The system according to claim 9, wherein the at least one measured physical characteristic is a torque required to change the rotational speed of the centrifugal furnace from the first rotational speed to the second rotational speed, and the determining means ascertains the viscosity from a time varying of the torque required to change the rotational speed of the centrifugal furnace from the first rotational speed to the second rotational speed.

13. The system according to claim 9, wherein the at least one measured physical characteristic is a surface velocity of the melt at a predetermined radial position in the centrifugal furnace, and the determining means ascertains the viscosity from a time required for the surface velocity to equal the rotational velocity of the centrifugal furnace at the predetermined radial position.

14. The system according to claim 9, wherein the at least one measured physical characteristic is a slope of a surface of the melt in the centrifugal furnace, and the determining means ascertains the viscosity from a time variation of the slope in the molten melt during the transition from the first rotational speed to the second rotational speed.

15. The system according to claim 9, wherein the at least one measured physical characteristic is a surface height of the melt, and the determining means ascertains the viscosity from a change in height of the molten melt during the transition from the first rotational speed to the second rotational speed.

16. The system according to claim 9, wherein the at least one measured physical characteristic is a diameter of a dry circle, and the step of determining the velocity ascertains the viscosity from a change in the diameter of a dry circle in the molten melt in the bottom of the rotating vessel during the transition from the first rotational speed to the second rotational speed.

* * * * *